United States Patent
Wu et al.

(10) Patent No.: US 11,771,562 B2
(45) Date of Patent: Oct. 3, 2023

(54) BALLOON, MEDICAL DEVICE AND MEDICAL PROCEDURE FOR DISCOPLASTY

(71) Applicant: The Second Affiliated Hospital and Yuying Children's Hospital of Wenzhou Medical University, Zhejiang (CN)

(72) Inventors: Aimin Wu, Wenzhou (CN); Xiangyang Wang, Wenzhou (CN); Yan Lin, Wenzhou (CN); Wenfei Ni, Wenzhou (CN); Zhongke Lin, Wenzhou (CN); Qishan Huang, Wenzhou (CN); Fangmin Mao, Wenzhou (CN); Sheng Wang, Wenzhou (CN)

(73) Assignee: THE SECOND AFFILIATED HOSPITAL AND YUYING CHILDREN'S HOSPITAL OF WENZHOU MEDICAL UNIVERSITY, Zhejiang (CN)

( * ) Notice: Subject to any disclaimer, the term of this patent is extended or adjusted under 35 U.S.C. 154(b) by 336 days.

(21) Appl. No.: 17/160,395

(22) Filed: Jan. 28, 2021

(65) Prior Publication Data

US 2022/0233317 A1    Jul. 28, 2022

(51) Int. Cl.
*A61F 2/44* (2006.01)
*A61B 17/88* (2006.01)
(Continued)

(52) U.S. Cl.
CPC .......... *A61F 2/441* (2013.01); *A61B 17/8808* (2013.01); *A61B 17/8816* (2013.01);
(Continued)

(58) Field of Classification Search
CPC ............ A61B 17/8805; A61B 17/8816; A61B 17/8855; A61F 2002/30586; A61F 2/441; A61F 2/4601
See application file for complete search history.

(56) References Cited

U.S. PATENT DOCUMENTS 6,332,894 B1 * 12/2001 Stalcup ................. A61F 2/4601
                                                   623/17.11
8,043,381 B2 * 10/2011 Hestad .................... A61F 2/441
                                                      606/90
(Continued)

FOREIGN PATENT DOCUMENTS

CN        112137707 A    * 12/2020  ......... A61B 17/7097
CN        112168325 A    *  1/2021  ......... A61B 17/7097
(Continued)

*Primary Examiner* — Larry E Waggle, Jr.
(74) *Attorney, Agent, or Firm* — Leong C. Lei

(57) ABSTRACT

A balloon, a medical device, and a medical procedure for discoplasty are disclosed. The balloon has a compressed, collapsed or folded balloon body containing a first chamber for, in use, receiving injected bone cement. With the bone cement filled and cured therein, the balloon acts as a support in tissue of an intervertebral disc while preventing the bone cement from leakage and dispersion. The deployed balloon body defines a second chamber running therethrough. The second chamber is configured to receive a material or cells that activate osteogenesis and/or osteo-induction, so that the material or cells injected into the second chamber through a second sprue form osteocytes or induce human spontaneous local cellular differentiation to in turn form osteocytes in the cavity of the intervertebral disc and connect vertebrae above and below the intervertebral disc, thereby securely anchoring the balloon within the intervertebral space.

2 Claims, 11 Drawing Sheets

(51) Int. Cl.
A61F 2/30 (2006.01)
A61F 2/46 (2006.01)

(52) U.S. Cl.
CPC ...... *A61B 17/8822* (2013.01); *A61F 2/30723* (2013.01); *A61F 2/30767* (2013.01); *A61F 2/4601* (2013.01); *A61F 2002/3093* (2013.01); *A61F 2002/30586* (2013.01)

(56) References Cited

U.S. PATENT DOCUMENTS 9,662,152 B2 * 5/2017 Riley ................. A61B 17/7097
2018/0193158 A1 * 7/2018 Suddaby ................. A61F 2/441

FOREIGN PATENT DOCUMENTS

CN 112137707 A * 2/2023
CN 112168325 A * 2/2023

* cited by examiner

BALLOON, MEDICAL DEVICE AND MEDICAL PROCEDURE FOR DISCOPLASTY

BACKGROUND OF THE INVENTION

1. Technical Field

The present invention relates to medical instruments, and more particularly to a balloon, a medical device and a medical procedure for discoplasty.

2. Description of Related Art

Percutaneous cement discoplasty (PCD) was first reported in 2015 by P.P. Varga (Hungary) in Orthopade.

PCD has been an effective minimally invasive method for dealing with axial low back pain and dysfunction caused by serious lumbar intervertebral disc degenerative diseases. PCD also helps to correct deformity of lumbar vertebrae, and provide indirect decompression for intervertebral foramen. This is particularly usable for elderly patients to whom open surgery is hard to perform. PCD can significantly decrease patients' sacral inclination angle and pelvic inclination angle, significantly improve segmental and global lumbar kyphosis, and increase the heights of treated intervertebral discs and intervertebral foramens. In experiments, the rating results of VAS and ODI noticeably improved, and the improvement of lumbago showed clear association with correction of segmental scoliosis, without obvious complications observed.

However, there is still a probability of bone cement leakage during PCD. Theoretically, bone cement leakage may cause compression to nerve roots or spinal cords.

In addition, since bone cement and human tissues are not combined well biologically, the connection between bone cement and primary intervertebral tissue can degrade deteriorate and loosen over time.

SUMMARY OF THE INVENTION

An objective of the present invention is to overcome the defects and shortcomings of the prior art by providing a balloon, a medical device and a medical procedure for discoplasty.

In one aspect of the present invention, a balloon for discoplasty comprises a compressed, collapsed or folded balloon body, which contains therein a first chamber, and has a surface provided with a first sprue communicated with the first chamber, wherein when deployed, the balloon body defines a second chamber running therethrough and has a medium inlet channel communicated with the second chamber, in which the balloon body has the surface further provided with a second sprue that is communicated with the medium inlet channel.

The balloon body is made of stacked inner and outer layers of a flexible material, and an expansion chamber is formed between the inner and outer layers of the flexible material, in which the outer layer of the flexible material is provided with a pressurizing port that is communicated with the expansion chamber, and a predetermined area between the inner and outer layers of the flexible material is provided with a connecting portion connecting the inner and outer layers of the flexible material, so that filling a pressurized medium into the expansion chamber through the pressurizing port such deploys the balloon body that the deployed balloon body has a ring-like shape with the ring-like first chamber defined therein.

The deployed balloon body has anti-slip bulges and/or grooves distributed across the surface thereof.

The balloon body is made of a polymer and/or a flexible metal.

The balloon body is at least partially degradable.

In a second aspect of the present invention, a medical device for discoplasty comprises:

the balloon for discoplasty as described previously, a first duct, communicated with the first sprue of the balloon; and a second duct, communicated with the second sprue of the balloon.

The surface of the balloon body is raised to form a third duct connected to a peripheral wall of the first sprue and a fourth duct connected to a peripheral wall of the second sprue, in which the first duct and the third duct are detachably connected, while the second duct and the fourth duct are detachably connected.

The third duct and the fourth duct each at least have a part near an outer end thereof made of a rigid material; and the first duct and the second duct are both made of a rigid material, an end of the first duct abutting against the outer end of the third duct, and an end of the second duct abutting against the outer end of the fourth duct.

The third duct is screwedly connected to the first duct and/or the fourth duct is screwedly connected to the second duct.

The third duct is sleeved around the fourth duct, and the fourth duct has an inner passage formed as a channel for feeding a medium into the second sprue, while a channel for feeding a further medium into the first sprue is formed between an inner wall of the third duct and an outer wall of the fourth duct;

the first duct being sleeved around the second duct, the second duct having an inner passage that forms a channel for feeding the medium into the fourth duct, and a channel being formed between an inner wall of the first duct and an outer wall of the second duct for filling the further medium between the inner wall of the third duct and the outer wall of the fourth duct; and the third duct being screwedly connected to the first duct or the fourth duct being screwedly connected to the second duct.

The fourth duct is provided therein with a plug for preventing the medium from flowing out.

The plug is a bolt configured to be screwedly engaged with the fourth duct, and the bolt has an outer end provided with a non-rotatable notch or knob for driving the bolt.

The plug is a check valve fixedly installed in the fourth duct.

The balloon body is made of stacked inner and outer layers of a flexible material, and an expansion chamber is formed between the inner and outer layers of the flexible material, in which the outer layer of the flexible material is provided with a pressurizing port that is communicated with the expansion chamber, and a predetermined area between the inner and outer layers of the flexible material is provided with a connecting portion connecting the inner and outer layers of the flexible material, so that filling a pressurized medium into the expansion chamber through the pressurizing port such deploys the balloon body that the deployed balloon body has a ring-like shape with the ring-like first chamber defined therein; and the balloon body further has a fifth duct that is communicated with the pressurizing port of the balloon.

The surface of the balloon body is raised to form a third duct connected to a peripheral wall of the first sprue, a fourth duct connected to a peripheral wall of the second sprue, and a sixth duct connected to a peripheral wall of the pressurizing port, in which the first duct and the third duct are detachably connected, and the second duct and the fourth duct are detachably connected, while the fifth duct and the sixth duct are detachably connected.

The third duct, the fourth duct and the sixth duct each at least have a part near an outer end thereof made of a rigid material;

the first duct, the second duct and the fifth duct all being made of a rigid material, an end of the first duct abutting against an outer end of the third duct, and an end of the second duct abutting against the outer end of the fourth duct; and the third duct being screwedly connected to the first duct and/or the fourth duct being screwedly connected to the second duct and/or the sixth duct being screwedly connected to the fifth duct.

The third duct is sleeved around the fourth duct, and the sixth duct is sleeved around the third duct, the fourth duct having an inner passage formed as a channel for feeding the medium into the second sprue, a channel for feeding the further medium into the first sprue being formed between an inner wall of the third duct and an outer wall of the fourth duct, and a channel for feeding the pressurized medium into the pressurizing port being formed between an inner wall of the sixth duct and an outer wall of the third duct; and the first duct being sleeved around the second duct, the fifth duct being sleeved around the first duct, the second duct having an inner passage that forms a channel for feeding the medium into the fourth duct, and a channel being formed between an inner wall of the first duct and an outer wall of the second duct for filling the further medium between the inner wall of the third duct and the outer wall of the fourth duct; and a channel for filling the pressurized medium between an inner wall of the sixth duct and an outer wall of the third duct being formed between an inner wall of the fifth duct and an outer wall of the first duct.

A medical procedure for discoplasty, uses the balloon for discoplasty as described above and comprises steps of:

(1) filling bone cement into the first chamber;

(2) aligning openings at two ends of the second chamber with intervertebral disc tissue at two sides of the balloon; and (3) filling the second chamber with a material or cells activating osteogenesis and/or osteo-induction;

wherein, the steps (1)-(3) are performed sequentially.

The balloon has a balloon body made of stacked inner and outer layers of a flexible material, and an expansion chamber is formed between the inner and outer layers of the flexible material, in which the outer layer of the flexible material is provided with a pressurizing port that is communicated with the expansion chamber, and a predetermined area between the inner and outer layers of the flexible material is provided with a connecting portion connecting the inner and outer layers of the flexible material, so that filling a pressurized medium into the expansion chamber through the pressurizing port such deploys the balloon body that the deployed balloon body has a ring-like shape with the ring-like first chamber defined therein; and the medical procedure for discoplasty further comprising a step of:

(4) filling the expansion chamber with the pressurized medium to deploy the balloon body;

wherein the step (4) is performed prior to the step (1).

the surface of the balloon body of the used balloon is raised to form a fourth duct connected to a peripheral wall of the second sprue, and the fourth duct is provided therein with a plug for preventing a medium from flowing out, in which the plug is a bolt configured to be screwedly engaged with the fourth duct, and the bolt has an outer end provided with a non-rotatable notch or knob for driving the bolt;

the medical procedure for discoplasty further comprising steps of:

(5) rotating the bolt to separate the bolt from the fourth duct; and (6) rotating the bolt to connect the bolt with the fourth duct;

wherein, the step (5) is performed prior to the step (3), and is independent of the step (1) and the step (2) in terms of sequence; and wherein, the step (6) is performed after the step (3).

The present invention has the following beneficial effects. The disclosed balloon uses the first chamber to receive bone cement injected therein. With the bone cement filled and cured therein, the balloon acts as a support in tissue of an intervertebral disc while preventing the bone cement from leakage and dispersion.

The second chamber is configured to receive the material activating osteogenesis and/or osteo-induction, so that the material injected into the second chamber through a second sprue form osteocytes or induce human spontaneous local cellular differentiation to in turn form osteocytes in the cavity of the intervertebral disc, thereby securely anchoring the balloon within the intervertebral space.

BRIEF DESCRIPTION OF THE DRAWINGS

In order to better illustrate technical features of embodiments of the present invention or of the prior art, brief introduction to accompanying drawings used to describe embodiments of the present invention or of the prior art are provided below. Apparently, the accompanying drawings listed below merely refer to some but not all embodiments of the present invention. For those of ordinary skill in the art, more drawings can be derived from these drawings without paying creative efforts, and all these derived drawings will be part of the scope of the present invention.

DETAILED DESCRIPTION OF THE INVENTION

For further illustrating the means and functions by which the present invention achieves the certain objectives, the following description, in conjunction with the accompanying drawings and preferred embodiments, is set forth as below to illustrate the implement, structure, features and effects of the subject matter of the present invention.

It is to be noted that, throughout the description of the present invention, where an ordinal number such as "first," or "second" is used, it is intended to differentiate two different entities with the same name or non-identical parameters, so such ordinal numbers are used merely for easy representation and shall not be understood as being limiting to embodiments of the present invention. In subsequent embodiments, no further explanation will be given for this.

In the description below, where a direction or a position is described using terms such as "upper," "lower," "front," "back," "left," "right," "inner," "outer," "top," "bottom," and "lateral," it refers to the direction or position shown in the accompany drawings. Therefore, these directional and positional descriptions are for explaining and understanding the present invention only, but not limiting the scope of the present invention.

Embodiment 1

Figure 1:
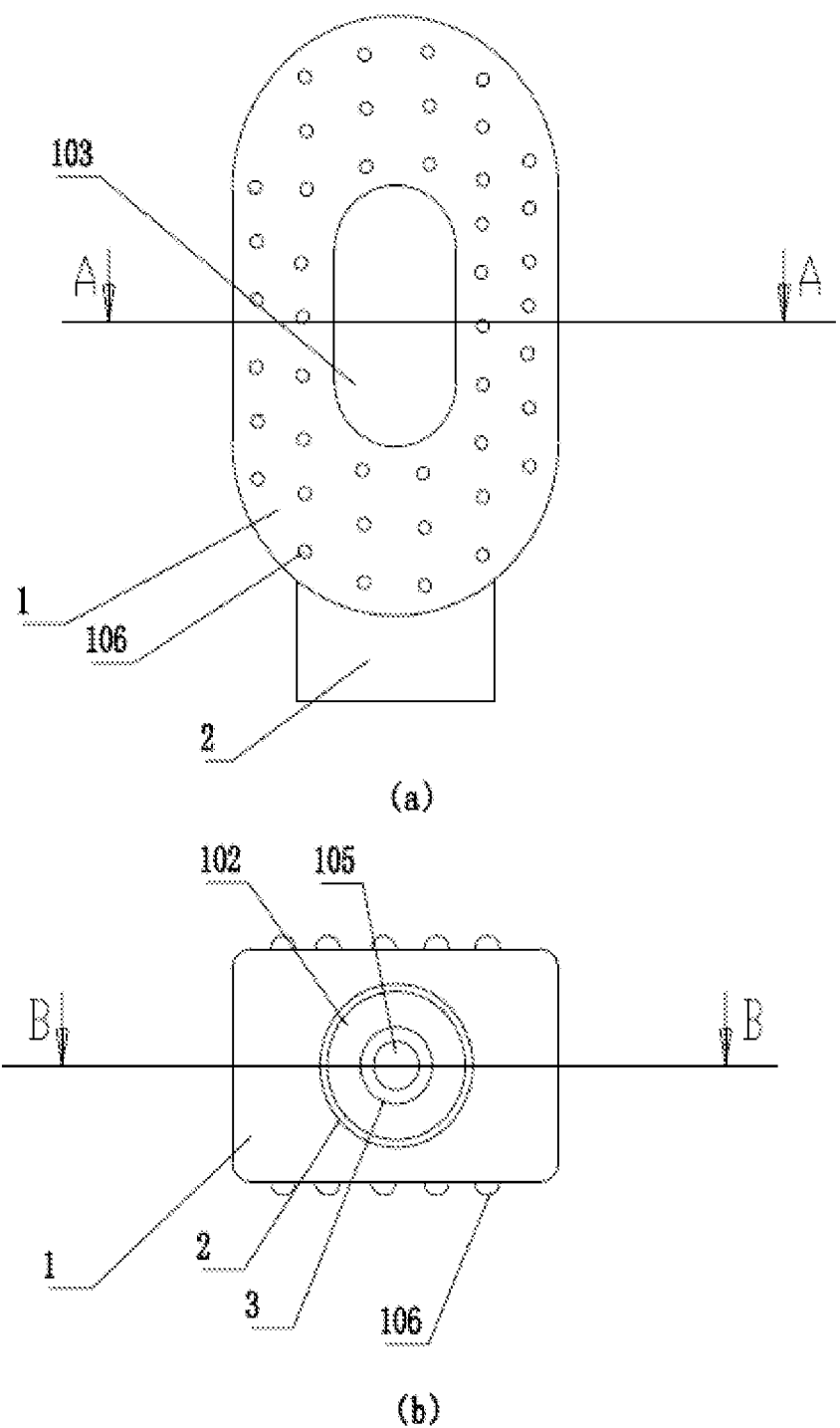
FIG. 1 schematically depicts a deployed balloon body according to a first embodiment of the present invention, and includes: (a) a top view, and (b) a front view.
Figure 2:
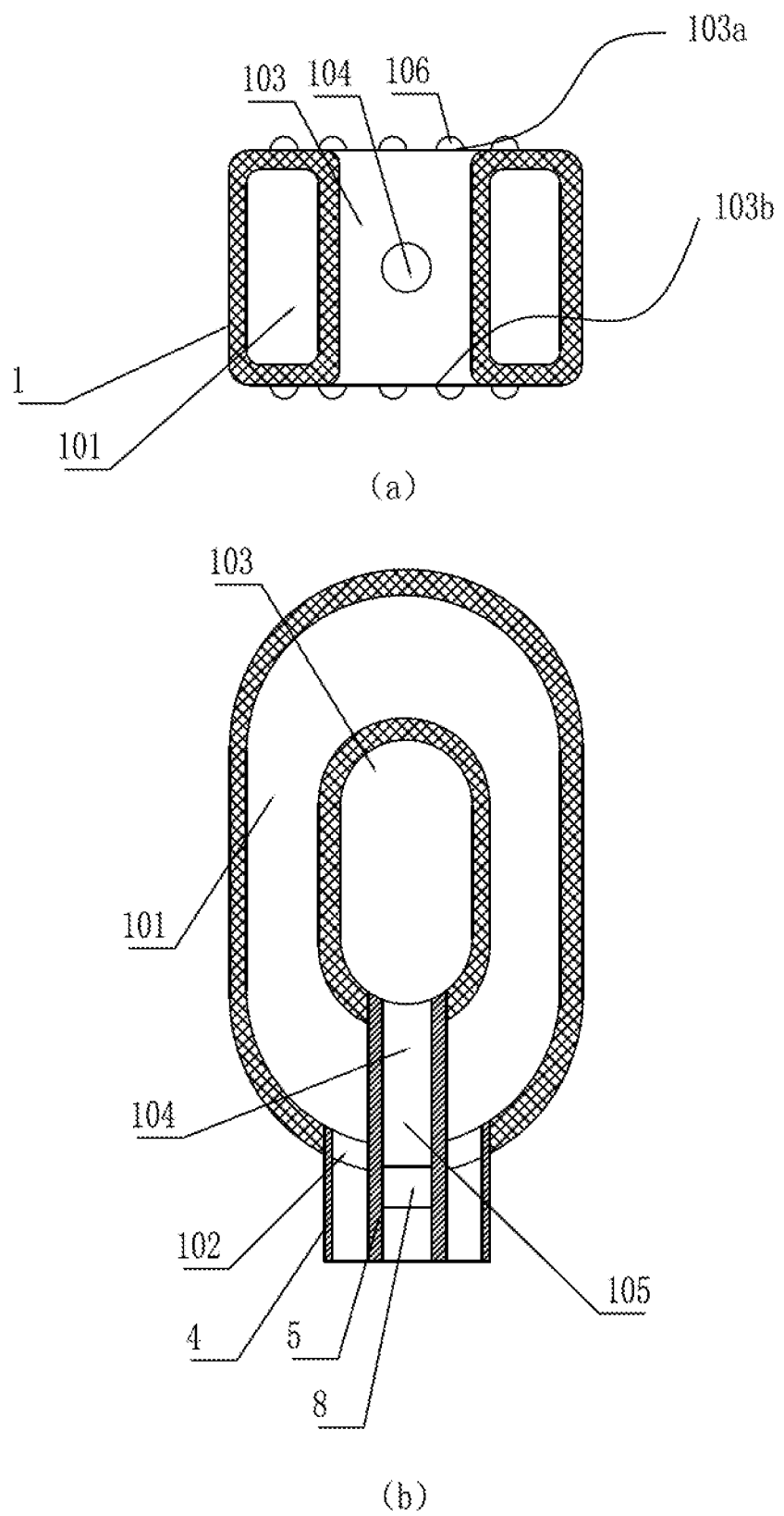
FIG. 2 includes cross-sectional views of the first embodiment, including: (a) a cross-sectional view taken along Line A-A in FIG. 1, and (b) a cross-sectional view taken along Line B-B in FIG. 1.

As shown in FIG. 1 and FIG. 2, a balloon for discoplasty comprises a compressed, collapsed or folded balloon body 1. The balloon body 1 is provided therein with first chamber 101. The balloon body 1 has its surface provided with a first sprue 102 that is communicated with the first chamber 101. By injecting a medium into the first chamber 101 through the first sprue 102, the balloon body 1 is deployed, or expanded, from the original compressed, collapsed or folded state.

After deployed, the balloon body 1 contains a second chamber 103 running therethrough. The balloon body 1 is provided therein with a medium inlet channel 104 communicated with the second chamber 103. On the surface of the balloon body 1, there is a second sprue 105 communicated with the medium inlet channel 104.

The first chamber 101 is configured to receive injected bone cement. After filled with bone cement, the balloon is deployed. The deployed balloon has an ellipse-like sectional shape. The balloon encloses and hold the bone cement from leakage and dispersion. After the bone cement is cured in the first chamber 101, the balloon forms a support with a fixed shape within the intervertebral space.

In the deployed balloon, the second chamber 103 is centrally or eccentrically located and runs through the balloon body 1 in its axial direction. The balloon body 1 has the medium inlet channel 104 communicated with the second chamber 103 and extending in a direction perpendicular to or inclined with respect to the axis of the balloon body 1. The balloon body 1 has its surface provided with the second sprue 105 communicated with the medium inlet channel 104. The second chamber 103 is for a material that activates osteogenesis and/or osteo-induction to pass therethrough during injection of the material. After the balloon is deployed by filling bone cement therein, the material that activates osteogenesis and/or osteo-induction can be injected to the second chamber 103 running through the balloon body 1 by way of the second sprue 105. The material injected into the second chamber 103 then forms osteocytes or induces human spontaneous local cellular differentiation to in turn form osteocytes in the cavity of the intervertebral disc, thereby securely anchoring the balloon within the intervertebral space.

The first sprue 102 and the second sprue 105 are both formed on the lateral surface of the balloon body 1.

Specifically, the material activating osteogenesis and/or osteo-induction may be one or more of living cells having osteogenesis capability such as myelocytes and/or a protein having osteo-induction capability such as demineralized bone matrix, bone morphogenetic protein, and growth factor. What is injected into the second chamber 103 may be in the form of solid powder, solid-liquid mixture, or liquid.

Anti-slip bulges 106 and/or grooves are distributed across the surface of the deployed balloon body 1. The anti-slip bulges 106 and/or grooves are of a shape that can increase the specific surface area and/or friction, such as a wave-like shape, a serrate shape, a spiral shape, a needle-like shape, a bar-like shape, or a figure. The figure may be one or a combination of round, ellipse, regular polygon, an irregular polygon, and an irregular figure. In the depicted embodiment, the bulges are anti-slip features. Specifically, the bulges may be formed by the variable thickness of the balloon body 1, which means the thickness of the balloon body 1 at sites where the bulges are formed is greater than the thickness at the rest of the balloon body 1. Alternative, the bulges may be exteriorly formed on the balloon body 1 having a constant thickness, so that when the balloon body 1 is expanded by the injected bone cement, the bulges appear at the surface of the balloon body 1.

The balloon body 1 is made of a polymer and/or a flexible metal.

Specifically, the balloon body 1 may be formed from an elastic film made of a polymer. The polymer may be one or more of elastomeric polymers, such as polyethylene terephthalate, polyamide, or polyether block amide, polyethylene, polyurethane, polyether polyurethane, polylactide, polycaprolactone, polyglycolide, poly(lactic-co-glycolic acid), and poly(lactic acid)-poly(ε-caprolactone) multi-block copolymer. The balloon made of the foregoing polymer material(s) is an expandable balloon, which gradually expands in response to its increasing internal pressure.

Specifically, the balloon body 1 may be a flexible metal net that is woven or crocheted from flexible metal wires and has small meshes to prevent permeation and leakage. Before being filled with bone cement, the flexible metal is collapsed or folded, and the bulges may be formed by varying the thickness. Particularly, the bulges may be formed by adding the number of woven layers during the weaving process so that some parts of the surface raise from others. Alternatively, hollow beads are woven into the net so that some parts of the surface raise from others. Further alternatively, the woven net is subsequently processed to have knots attached to the surface by means of adhesion or welding. As yet another alternative, bulges are formed on the surface by means of electroplating or electroforming. The flexible metal wires may be made of gold, silver, titanium or an alloy or a combination thereof.

Specifically, the balloon body 1 may be a complex of an inner layer and an outer layer. The two layers are a flexible metal net layer woven or crocheted from flexible metal wires and having large meshes and an elastic film layer made of a polymer, with either one inside the other. The elastic film layer made of the polymer may be a continuous film layer or a non-continuous film layer. The elastic film layer and the flexible metal net layer may be bound using an adhesive. Preferably, the elastic film layer is arranged inside the flexible metal net layer.

The balloon body 1 is at least partially degradable. After the balloon is degraded in a human body, calcium ions in the bone cement can be released to liquid. In the present embodiment, the flexible metal net layer and the elastic film layer are combined to form the balloon body 1, with the elastic film layer arranged outside. The flexible metal net layer endows the balloon with good strength. After the degradable polymer is degraded, calcium ions in the bone cement are released to liquid through the large meshes of the metal net layer.

The degradable polymer may be one of or a polymerblend of polylactide, polycaprolactone, polyglycolide, poly(lactic-co-glycolic acid), poly(lactic acid)-poly(ε-caprolactone) multi-block copolymer, chitosan, sodium alginate, polyethylene glycol, polyglycolide, polyaspartic acid, sodium carboxymethyl cellulose, hydroxy propyl methyl cellulose, polyethylene glycol, polyether, and poly(lactic-co-glycolic acid.

As shown in FIG. 1(*b*) and FIG. 2(*b*), the surface of the balloon body 1 is raised to form a third duct 4 connected to the peripheral wall of the first sprue 102 and a fourth duct 5 connected to the peripheral wall of the second sprue 105. The third duct 4 is sleeved around the fourth duct 5. The inner passage of the fourth duct 5 forms a channel for introducing the medium to the second sprue 105. Between the inner wall of the third duct 4 and the outer wall of the fourth duct 5, a channel for introducing the medium to the first sprue 102 is formed.

Embodiment 2

Figure 3:
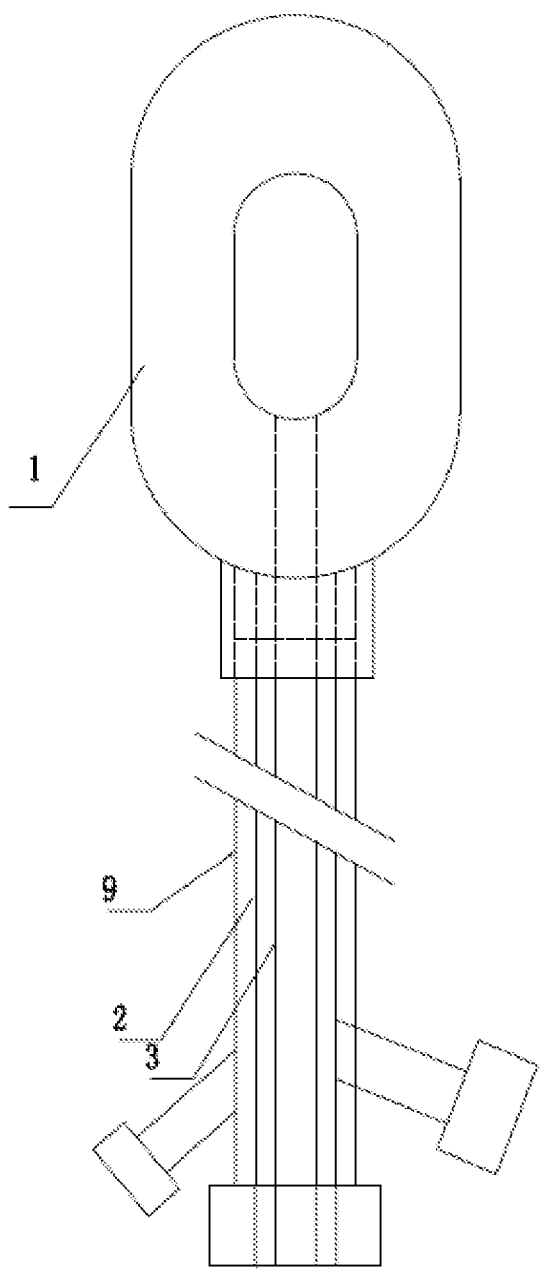
FIG. 3 is a schematic structural drawing of a second embodiment of the present invention.

As shown in FIG. 3, a medical device for discoplasty comprises a balloon as that described in Embodiment 1, a first duct 2 communicated with the first sprue 102 of the balloon, and a second duct 3 communicated with the second sprue 105 of the balloon. In use, bone cement is injected into the first chamber 101 through the first duct 2 and the material activating osteogenesis and/or osteo-induction is injected into the second chamber 103 through the second duct 3.

The material activating osteogenesis and/or osteo-induction is specifically one or more of living cells having osteogenesis capability such as myelocytes and/or a protein having osteo-induction capability such as a demineralized bone matrix, a bone morphogenetic protein, and a growth factor.

Figure 4:
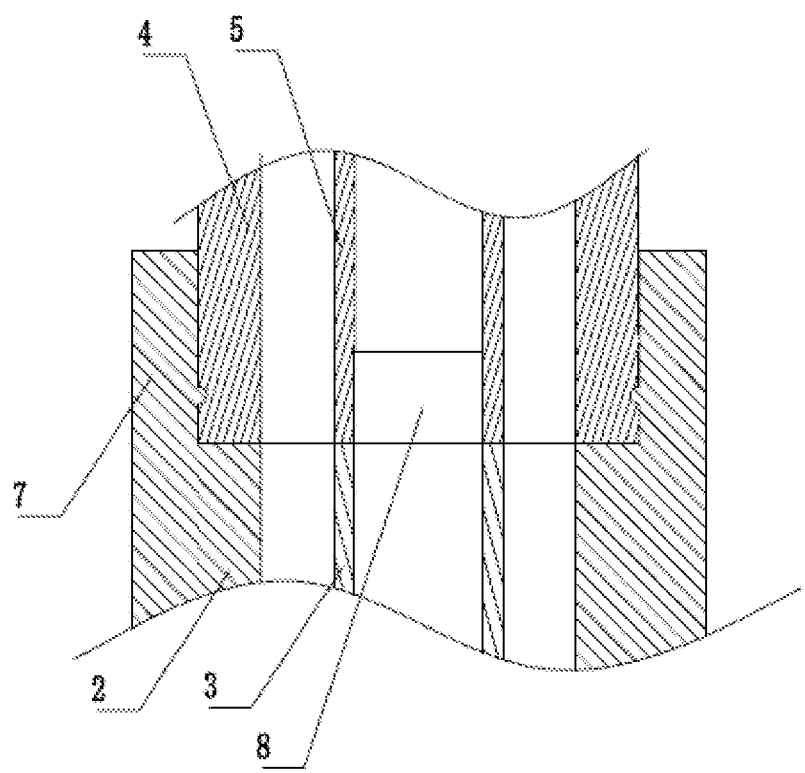
FIG. 4 is a schematic structural drawing showing joints among first, second, third and fourth ducts of the second embodiment.
Figure 5:
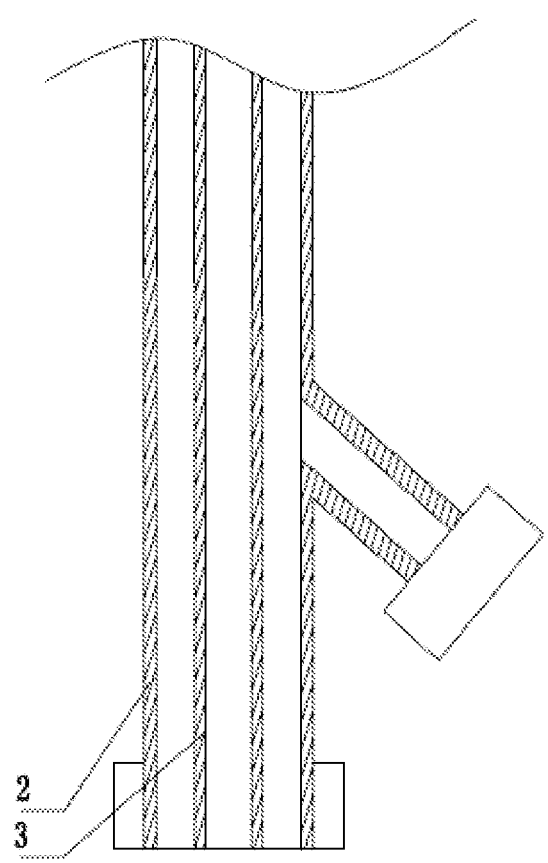
FIG. 5 is a schematic structural drawing of the second embodiment, showing ends of the first duct, the second duct, and a second pipe connecting member that are far from the third duct.

As shown in FIG. 4, the first duct 2 and the third duct 4 are detachably connected, while the second duct 3 and the fourth duct 5 are detachably connected. The first duct 2 is sleeved around the second duct 3. The inner passage of the second duct 3 forms a channel for introducing the medium to the fourth duct 5. Between the inner wall of the first duct 2 and the outer wall of the second duct 3, a channel for introducing the medium between the inner wall of the third duct 4 and the outer wall of the fourth duct 5 is formed.

The third duct 4 and the fourth duct 5 each at least have a part near an outer end thereof made of a rigid material. The third duct 4 and the fourth duct 5 are fixed with respect to each other. The first duct 2 and the second duct 3 are both made of a rigid material. The first duct 2 and the second duct 3 are fixed with respect to each other. The first duct 2 has its end abutting against the outer end of the third duct 4, and the second duct 3 has its end abutting against the outer end of the fourth duct 5.

The third duct 4 and the first duct 2 are screwedly connected to each other, or the fourth duct 5 and the second duct 3 are screwedly connected to each other. In the present embodiment, the first duct 2 is sleeved around the third duct 4 and the two are screwedly connected to each other.

Sealing members may be arranged at the joint between the third duct 4 and the first duct 2 and at the joint between the fourth duct 5 and the second duct 3 for enhancing airtightness and preventing leakage.

The fourth duct 5 is provided therein with a plug 8 for preventing the medium from flowing out. Specifically, the plug 8 may be a check valve fixedly installed in the fourth duct 5.

Alternatively, the plug 8 is a bolt screwedly connected to the fourth duct 5. The bolt has an outer end provided with a non-rotatable notch or knob for driving the bolt. The non-rotatable notch or knob may be specifically a polygonal notch or knob. In operation, before the material activating osteogenesis and/or osteo-induction is injected, the bolt is screwed out, and after the material activating osteogenesis and/or osteo-induction is injected, the bolt is screwed into the fourth duct 5 through the second duct 3.

Each of the first duct 2 and the second duct 3 has a connecting portion at or near its outer end, for connecting an injector that injects the material. Alternatively, the first duct 2 and the second duct 3 have their ends formed as injectors directly.

Figure 6:
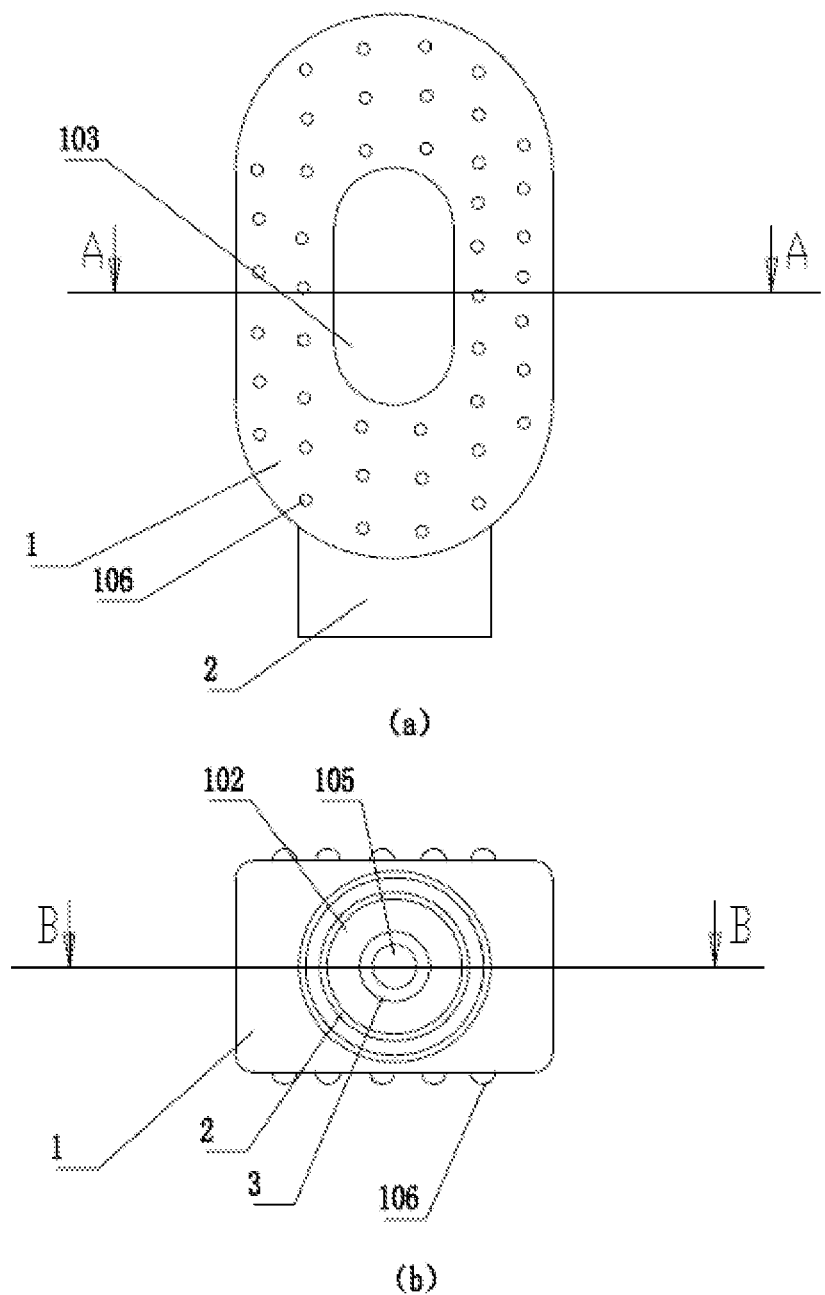
FIG. 6 includes schematic structural drawings of the deployed balloon body of a third embodiment of the present invention, including: (a) a top view, and (b) a front view.

Referring to FIG. 3, the depicted embodiment has a specific configuration as described below. The connecting portions at the outer ends of the first and second ducts 2, 3 are for connecting the injector as shown in FIG. 6 that injects the material into the second duct 3 or injects the material to the channel between the first duct 2 and the second duct 3. A pushing lever is configured to be pushed into the channel between the first duct 2 and the second duct 3 and into the channel in the second duct 3 through the outer ends of the first and second ducts 2, 3. At the lateral and near the outer end of the first duct 2, a connecting portion is provided to connect the injector that injects the material into the channel between the first duct 2 and the second duct 3.

Using the present embodiment for discoplasty may involve the following steps:

(1) placing the compressed, collapsed or folded balloon body 1 at a target site, and connecting the injector jacket 11 to the outer ends of the first and second ducts 2, 3;

(2) injecting bone cement into the first chamber 101 through the first duct 2, which is achieved by: injecting bone cement between the first duct 2 and the second duct 3; then pushing the bone cement into the first chamber 101 using a ring-shaped pushing lever matching the channel between the first duct 2 and the second duct 3; according to a preset amount of bone cement, more bone cement may be injected by operating the ring-shaped pushing lever 12 repeatedly; or injecting the preset amount of bone cement or slightly more than the preset amount of bone cement into the channel between the first duct 2 and the second duct 3 through the connecting portion at the lateral of the first duct 2; and finally pushing all or almost all of the bone cement (as some bone cement may remain in gaps around the ring-shaped pushing lever) into the balloon body 1 using the ring-shaped pushing lever;

(3) injecting the material activating osteogenesis and/or osteo-induction into the second chamber 103 through the second duct 3, which is achieved by: injecting the material activating osteogenesis and/or osteo-induction into the second duct 3; then pushing the material activating osteogenesis and/or osteo-induction into the first second chamber 103 using a post-shaped pushing lever matching the channel in the second duct 3; according to a preset amount of the material activating osteogenesis and/or osteo-induction, injecting bone cement in one time or in several batches using the post-shaped pushing lever 13, or injecting the preset amount or slightly more than the preset amount of the material activating osteogenesis and/or osteo-induction; and finally pushing all or almost all of the material activating osteogenesis and/or osteo-induction (as some material may remain in gaps around the post-shaped pushing lever) into the balloon body 1 using the post-shaped pushing lever 13;

wherein if the plug 8 is a check valve, the check valve can prevent the material activating osteogenesis and/or osteo-induction from flowing reversely, and if the plug 8 is a bolt, the bolt is screwed into the fourth duct 5 through the second duct 3 to prevent the material activating osteogenesis and/or osteo-induction from flowing reversely; and (4) when the bone cement is in the late dough phase and about to become cured, separating the first duct 2 from the third duct 4, retracting the first duct 2 and the third duct 4 from the human body, and leaving the balloon of Embodiment 1 together with the bone cement and the material activating osteogenesis and/or osteo-induction in the human body.

Therein, the bone cement injected in the step (2) may be in the thin phase, the drawing phase, or the early dough phase. Preferably, it is in the thin phase to give plenty time for operation.

According to the prior art, percutaneous kyphoplasty requires bone cement injected to be in the late drawing phase or the early dough phase. This is because if injection is performed with bone cement in the thin phase, the bone cement is more mobile, and tends to spread out. On the other hand, if injection is performed with bone cement in the late dough phase, the bone cement is insufficiently dispersible, and tends to cause duct blockage. With use of the balloon, the present embodiment eliminates the concern about leakage and dispersion of bone cement, and thereby allows the bone cement injected to be in the thin phase In the present embodiment, the balloon body 1 is deployed by injecting bone cement. However, the injected flow of bone cement may be not strong enough to enable the deployed balloon body 1 to provide satisfying reduction of the intervertebral disc to be treated. To address this concern, before use of the present embodiment, a cavity for receiving bone cement may be otherwise made in the intervertebral disc to be treated and after the intervertebral disc is satisfyingly reduced, the balloon body 1 is placed in position and bone cement is injected.

Embodiment 3

An expandable balloon for discoplasty comprises a compressed, collapsed or folded balloon body 1. The balloon body 1 is made of stacked inner and outer layers of a flexible material, and an expansion chamber 109 is formed between the inner and outer layers of the flexible material. The outer layer of the flexible material is provided with a pressurizing port 107 communicated with the expansion chamber 109. Between the inner and outer layers of the flexible material, there are some separate connecting portions 108 for connecting the inner and outer layers of the flexible material. The balloon body 1 can be expanded, or deployed, by filling a pressurized medium into the expansion chamber 109 through the pressurizing port 107.

Figure 7:
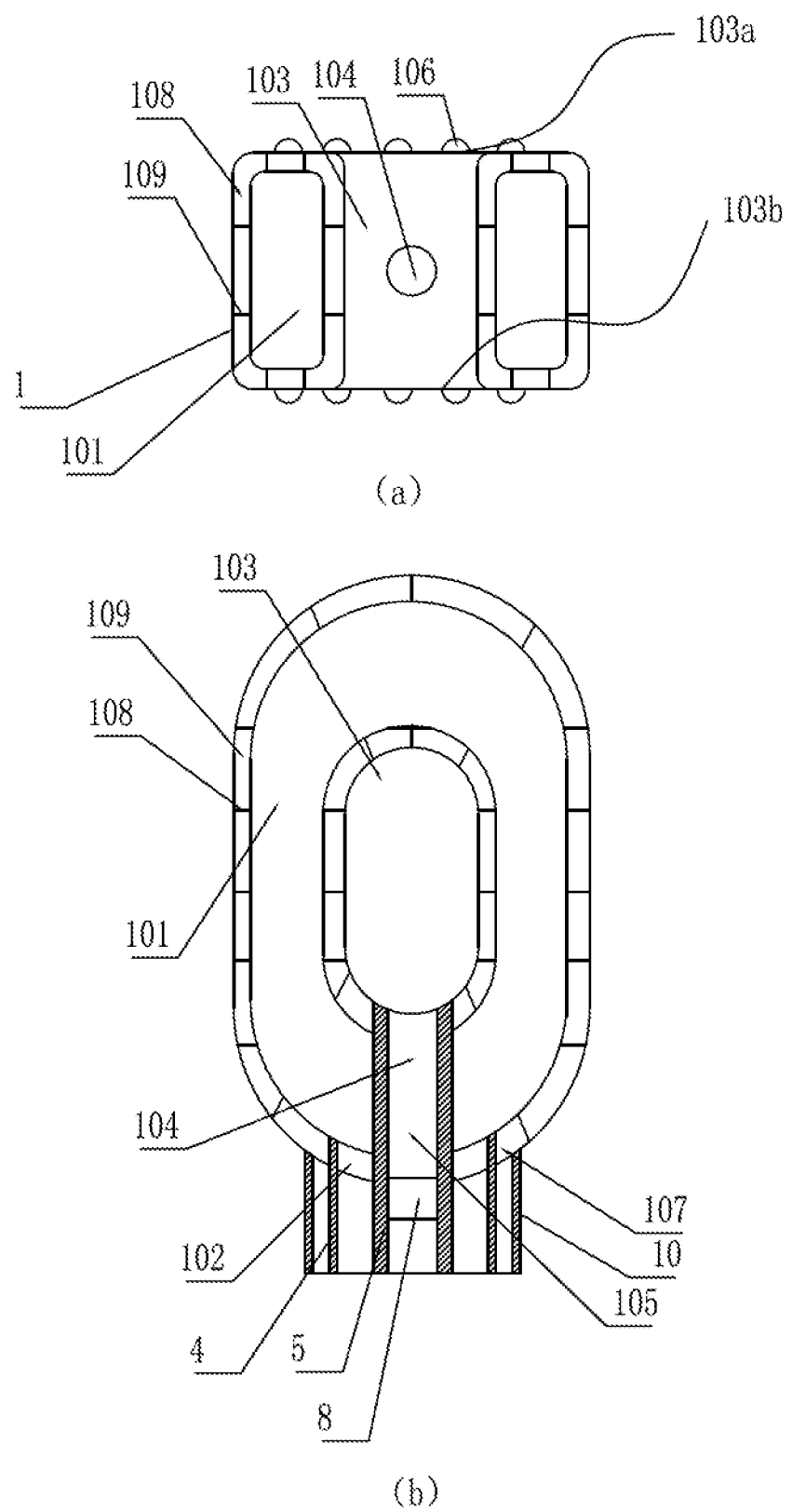
FIG. 7 includes cross-sectional views of the third embodiment, including (a) a cross-sectional view taken along Line A-A in FIG. 1, and (b) a cross-sectional view taken along Line B-B in FIG. 1.

After deployed, the balloon body 1, as shown in FIG. 6 and FIG. 7, has a ring-like shape. The balloon body 1 is provided therein with a first chamber 101, and has its surface provided with a first sprue 102 communicated with the first chamber 101. By injecting a medium into the first chamber 101 through the first sprue 102, the balloon body 1 is deployed, or expanded, from the original compressed, collapsed or folded state.

After deployed, the balloon body 1 contains a second chamber 103 running therethrough. The balloon body 1 is provided therein with a medium inlet channel 104 communicated with the second chamber 103. On the surface of the balloon body 1, there is a second sprue 105 communicated with the medium inlet channel 104.

In the present embodiment, the balloon body 1 is an expandable balloon body composed of inner and outer layers of a flexible material and having connecting portions 108 at local sites for connecting the inner and outer layers of the flexible material so as to ensure that the inner and outer layers of the flexible material remain connected after the balloon body 1 is expanded. In the expanded balloon body 1, the first chamber 101 and the second chamber 103 are increased in volume for receiving bone cement and the material activating osteogenesis and/or osteo-induction, respectively. The air pressure or hydraulic pressure is high enough to allow the balloon body to be fully expanded in the intervertebral disc. The pressurized medium may be a gas such as air or nitrogen gas, or may be water or an X-ray impermeable contrast medium. Preferably, the balloon body is expanded by filling air or an X-ray impermeable contrast medium.

The connecting portions are only arranged at select sites between the inner and outer layers of the flexible material without hindering formation of the continuous expansion chamber between the inner and outer layers of the flexible material. The structure and number of the connecting portions are such controlled that the inner and outer layers of the flexible material of the inflated balloon body are relatively close in distance. Each of the connecting portions may be integratedly formed with the inner and outer layers of the flexible material, or may be a link installed between the inner and outer layers of the flexible material with its two ends fixed to the inner and outer layers of the flexible material, respectively.

The expanded balloon has a ring-like shape. While it is ellipse-like in the drawings to better fit the central part of an intervertebral disc, it may be alternatively be round or square. The second chamber 103 is centrally or eccentrically located and runs through the balloon body 1 in its axial direction. The balloon body 1 has the medium inlet channel 104 communicated with the second chamber 103 and extending in a direction perpendicular to or inclined with respect to the axis of the balloon body 1. The balloon body 1 has its surface provided with the second sprue 105 communicated with the medium inlet channel 104. The second chamber 103 is for a material that activates osteogenesis and/or osteo-induction to pass therethrough during injection of the material. After the balloon is deployed by filling bone cement therein, the material that activates osteogenesis and/or osteo-induction can be injected to the second chamber 103 running through the balloon body 1 by way of the second sprue 105. The material injected into the second chamber 103 then forms osteocytes or induces human spontaneous local cellular differentiation to in turn form osteocytes in the cavity of the intervertebral disc, thereby securely anchoring the balloon within the intervertebral space.

The first sprue 102 and the second sprue 105 are both arranged on the lateral surface of the balloon body 1.

The material activating osteogenesis and/or osteo-induction is specifically one or more of living cells having osteogenesis capability such as myelocytes and/or a protein having osteo-induction capability such as a demineralized bone matrix, a bone morphogenetic protein, and a growth factor. What is injected into the second chamber 103 may be in the form of solid powder, solid-liquid mixture, or liquid.

Anti-slip bulges 106 and/or grooves are distributed across the surface of the deployed balloon body 1. The anti-slip bulges 106 and/or grooves are of a shape that can increase the specific surface area and/or friction, such as a wave-like shape, a serrate shape, a spiral shape, a needle-like shape, a bar-like shape, or a figure. The figure may be one or a combination of round, ellipse, regular polygon, an irregular polygon, and an irregular figure. In the depicted embodiment, the bulges are anti-slip features. Specifically, the bulges may be formed by the variable thickness of the balloon body 1, which means the thickness of the balloon body 1 at sites where the bulges are formed is greater than the thickness at the rest of the balloon body 1. Alternative, the bulges may be exteriorly formed on the balloon body 1 having a constant thickness, so that when the balloon body 1 is expanded by the injected bone cement, the bulges appear at the surface of the balloon body 1.

The inner and outer layers of the balloon body 1 may be made of the same or different materials. Specifically, the material(s) may be a polymer and/or a flexible metal.

Specifically, the balloon body 1 may be formed from an elastic film made of a polymer. The polymer may be one or more of elastomeric polymers, such as polyethylene terephthalate, polyamide, or polyether block amide, polyethylene, polyurethane, polyether polyurethane, polylactide, polycaprolactone, polyglycolide, poly(lactic-co-glycolic acid), and poly(lactic acid)-poly(ε-caprolactone) multi-block copolymer. The balloon made of the foregoing polymer material(s) is an expandable balloon, which gradually expands in response to its increasing internal pressure.

Specifically, the balloon body 1 may be a flexible metal net that is woven or crocheted from flexible metal wires and has small meshes to prevent permeation and leakage. Before being filled with bone cement, the flexible metal is collapsed or folded, and the bulges may be formed by varying the thickness. Particularly, the bulges may be formed by adding the number of woven layers during the weaving process so that some parts of the surface raise from others. Alternatively, hollow beads are woven into the net so that some parts of the surface raise from others. Further alternatively, the woven net is subsequently processed to have knots attached to the surface by means of adhesion or welding. As yet another alternative, bulges are formed on the surface by means of electroplating or electroforming. The flexible metal wires may be made of gold, silver, titanium or an alloy or a combination thereof.

Specifically, the balloon body 1 may be a complex of an inner layer and an outer layer. The two layers are a flexible metal net layer woven or crocheted from flexible metal wires and having large meshes and an elastic film layer made of a polymer, with either one inside the other. The elastic film layer made of the polymer may be a continuous film layer or a non-continuous film layer. The elastic film layer and the flexible metal net layer may be bound using an adhesive. Preferably, the elastic film layer is arranged inside the flexible metal net layer.

The balloon body 1 is at least partially degradable. After the balloon is degraded in a human body, calcium ions in the bone cement can be released to liquid. In the present embodiment, the flexible metal net layer and the elastic film layer are combined to form the balloon body 1, with the elastic film layer arranged outside. The flexible metal net layer endows the balloon with good strength. After the degradable polymer is degraded, calcium ions in the bone cement are released to liquid through the large meshes of the metal net layer.

The degradable polymer may be one of or a polymerblend of polylactide, polycaprolactone, polyglycolide, poly(lactic-co-glycolic acid), poly(lactic acid)-poly(ε-caprolactone) multi-block copolymer, chitosan, sodium alginate, polyethylene glycol, polyglycolide, polyaspartic acid, sodium carboxymethyl cellulose, hydroxy propyl methyl cellulose, polyethylene glycol, polyether, and poly(lactic-co-glycolic acid).

As shown in FIG. 7(*b*), the surface of the balloon body 1 is raised to form a third duct 4 connected to the peripheral wall of the first sprue 102, a fourth duct 5 connected to the peripheral wall of the second sprue 105, and a sixth duct 10 connected to the peripheral wall of the pressurizing port 107. The third duct 4 is sleeved around the fourth duct 5. The sixth duct 10 is sleeved around the third duct 4. The inner passage of the fourth duct 5 forms a channel introducing the medium to the second sprue 105. A channel for introducing the medium to the first sprue 102 is formed between the inner wall of the third duct 4 and the outer wall of the fourth duct 5. A channel for introducing the medium to the pressurizing port 107 is formed between the inner wall of the sixth duct 10 and the outer wall of the third duct 4.

In the present embodiment, the third duct 4, the fourth duct 5, and the sixth duct 10 are specifically made of a rigid material. The rigid material may be a metal or a polymer. Alternatively, only the parts at the outer ends of the third, fourth and sixth ducts 4, 5, 10 are made of a rigid material.

Embodiment 4

Figure 8:
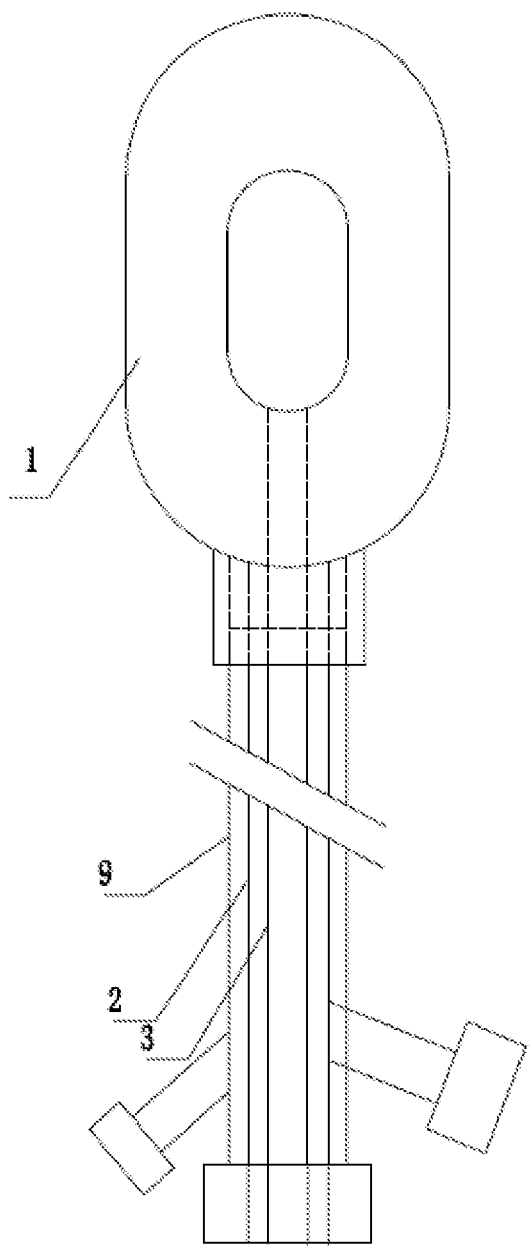
FIG. 8 is a schematic structural drawing of a fourth embodiment of the present invention.
Figure 9:
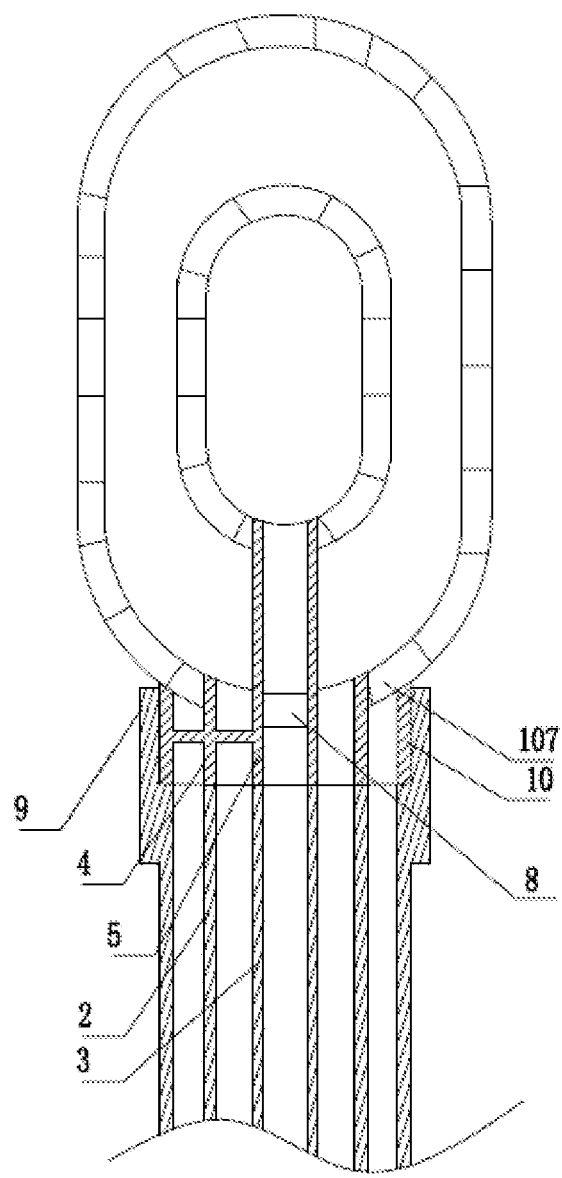
FIG. 9 is a schematic structural drawing of the fourth embodiment, showing joints among first, second, third, fourth, fifth and sixth ducts of the balloon body.
Figure 10:
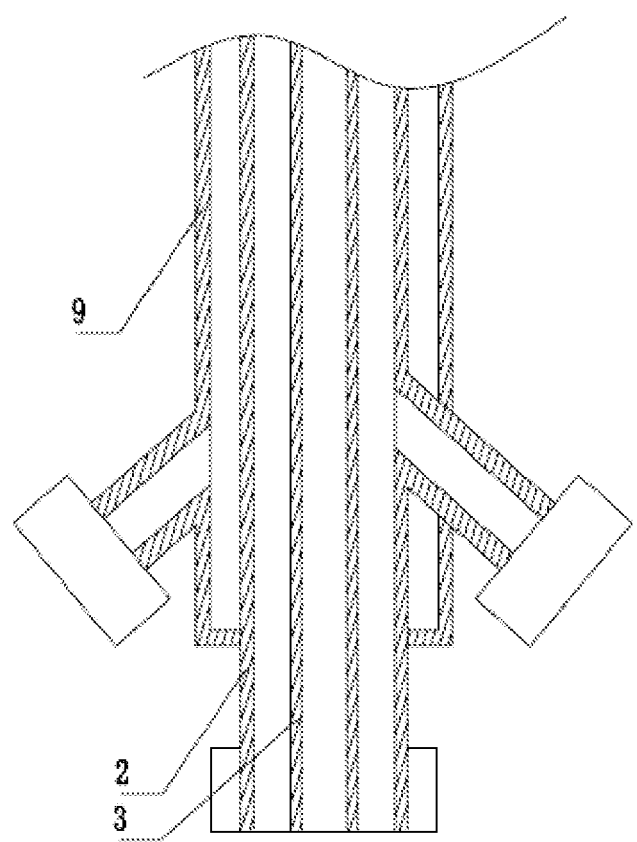
FIG. 10 is a schematic structural drawing of the fourth embodiment, showing ends of the first duct, the second duct, and the fifth duct that are far from the third duct.
Figure 11:
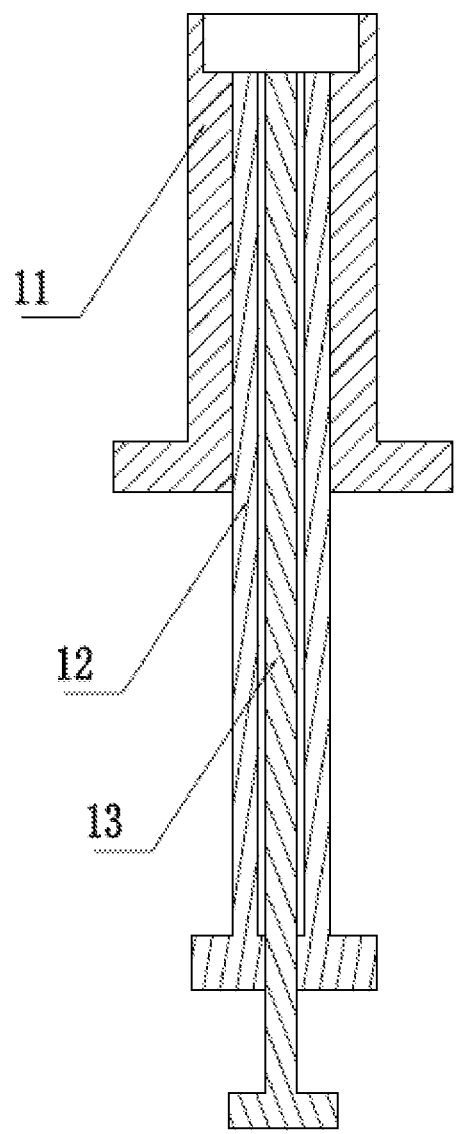
FIG. 11 is a schematic structural drawing of an injector.

As shown in FIGS. 8-10, a medical device for discoplasty comprises a balloon as that described in Embodiment 1, a first duct 2 communicated with the first sprue 102 of the balloon, a second duct 3 communicated with the second sprue 105 of the balloon; and a fifth duct 9 communicated with the pressurizing port 107 of the balloon. Bone cement is injected into the first chamber 101 through the first duct 2. The material activating osteogenesis and/or osteo-induction is injected into the second chamber 103 through the second duct 3. The gas is filled into the expansion chamber 109 of the balloon.

The material activating osteogenesis and/or osteo-induction is specifically one or more of living cells having osteogenesis capability such as myelocytes and/or a protein having osteo-induction capability such as demineralized bone matrix, bone morphogenetic protein, and growth factor.

As shown in FIG. 9, the first duct 2 and the third duct 4 are detachably connected to each other, and the second duct 3 and the fourth duct 5 are detachably connected each other, while the fifth duct 9 and the sixth duct 10 are detachably connected to each other. The first duct 2 is sleeved around the second duct 3, and the fifth duct 9 is sleeved around the first duct 2. The inner passage of the second duct 3 forms a channel for introducing the medium to the fourth duct 5. A channel is formed between the inner wall of the first duct 2 and the outer wall of the second duct 3 for introducing the medium between the inner wall of the third duct 4 and the outer wall of the fourth duct 5. A channel is formed between the inner wall of the fifth duct 9 and the outer wall of the first duct 2 for introducing the medium between the inner wall of the sixth duct 10 and the outer wall of the third duct 4.

The third duct 4, the fourth duct 5 and the sixth duct 10 each at least have a part near an outer end thereof made of a rigid material, and the third duct 4, the fourth duct 5 and the sixth duct 10 are fixed with respect to each other. The first duct 2, the second duct 3 and the fifth duct 9 are all made of a rigid material, and the first duct 2, the second duct 3 and the fifth duct 9 are fixed with respect to each other. The first duct 2 has its end abutting against the outer end of the third duct 4, and the second duct 3 has its end abutting against the outer end of the fourth duct 5, while the fifth duct 9 has its end abutting against the outer end of the sixth duct 10.

The third duct 4 and the first duct 2 are screwedly connected to each other or the fourth duct 5 and the second duct 3 are screwedly connected to each other or the sixth duct 10 and the fifth duct 9 are screwedly connected to each other. In the present embodiment, the fifth duct 9 is sleeved around the sixth duct 10 and the two are screwedly connected to each other.

Sealing members may be arranged at the joint between the third duct 4 and the first duct 2 and at the joint between the fourth duct 5 and the second duct 3 for enhancing airtightness and preventing leakage.

The fourth duct 5 is provided therein with a plug 8 for preventing the medium from flowing out. Specifically, the plug 8 may be a check valve fixedly installed in the fourth duct 5.

Alternatively, the plug 8 is a bolt screwedly connected to the fourth duct 5. The bolt has an outer end provided with a non-rotatable notch or knob for driving the bolt. The non-rotatable notch or knob may be specifically a polygonal notch or knob. In operation, before the material activating osteogenesis and/or osteo-induction is injected, the bolt is screwed out, and after the material activating osteogenesis and/or osteo-induction is injected, the bolt is screwed into the fourth duct 5 through the second duct 3.

Each of the first duct 2 and the second duct 3 has a connecting portion at or near its outer end, for connecting an injector that injects the material. Alternatively, the first duct 2 and the second duct 3 have their ends formed as injectors directly.

Referring to FIG. 8, the depicted embodiment has a specific configuration as described below. The connecting portions at the outer ends of the first and second ducts 2, 3 are for connecting the injector as shown in FIG. 6 that injects the material into the second duct 3 or injects the material to the channel between the first duct 2 and the second duct 3. A pushing lever is configured to be pushed into the channel between the first duct 2 and the second duct 3 and into the channel in the second duct 3 through the outer ends of the first and second ducts 2, 3. At the lateral and near the outer end of the first duct 2, a connecting portion is provided to connect the injector that injects the material into the channel between the first duct 2 and the second duct 3. At the lateral wall of the fifth duct 9, there is a pipe connecting portion for connecting the gas to be introduced.

Using the present embodiment for discoplasty may involve the following steps:

(1) placing the compressed, collapsed or folded balloon body 1 at a target site, and connecting the injector jacket 11 to the outer ends of the first and second ducts 2, 3;

(2) injecting a pressurized medium into the expansion chamber 109 of the balloon body 1 through the fifth duct 9, wherein the pressurized medium may be a gas such as air or nitrogen gas, or may be water or an X-ray impermeable contrast medium, to expand the balloon, in which during the injection it is important to keep the balloon centered in the intervertebral disc by rotating and/or moving the balloon so that two ends 103*a* and 103*b* of the second chamber 103 are aligned with the intervertebral disc tissue at two sides of the balloon body 1, and keep injecting the pressurized medium until the intervertebral disc is reduced satisfyingly;

(3) injecting bone cement into the first chamber 101 through the first duct 2, which is achieved by: injecting bone cement between the first duct 2 and the second duct 3; then pushing the bone cement into the first chamber 101 using a ring-shaped pushing lever matching the channel between the first duct 2 and the second duct 3; according to a preset amount of bone cement, more bone cement may be injected by operating the ring-shaped pushing lever 12 repeatedly; or injecting the preset amount of bone cement or slightly more than the preset amount of bone cement into the channel between the first duct 2 and the second duct 3 through the connecting portion at the lateral of the first duct 2; and finally pushing all or almost all of the bone cement (as some bone cement may remain in gaps around the ring-shaped pushing lever) into the balloon body 1 using the ring-shaped pushing lever;

(4) injecting the material activating osteogenesis and/or osteo-induction into the second chamber 103 through the second duct 3, which is achieved by: injecting the material activating osteogenesis and/or osteo-induction into the second duct 3; then pushing the material activating osteogenesis and/or osteo-induction into the first second chamber 103 using a post-shaped pushing lever matching the channel in the second duct 3; according to a preset amount of the material activating osteogenesis and/or osteo-induction, injecting bone cement in one time or in several batches using the post-shaped pushing lever 13, or injecting the preset amount or slightly more than the preset amount of the material activating osteogenesis and/or osteo-induction; and finally pushing all or almost all of the material activating osteogenesis and/or osteo-induction (as some material may remain in gaps around the post-shaped pushing lever) into the balloon body 1 using the post-shaped pushing lever 13;

wherein if the plug 8 is a check valve, the check valve can prevent the material activating osteogenesis and/or osteo-induction from flowing reversely, and if the plug 8 is a bolt, the bolt is screwed into the fourth duct 5 through the second duct 3 to prevent the material activating osteogenesis and/or osteo-induction from flowing reversely;

(5) when the bone cement is in the late dough phase and about to become cured, making the expansion chamber 109 release the pressurized medium; separating the fifth duct 9 from the sixth duct 10; retracting the first duct 2, the second duct 3 and the fifth duct 9 from the human body; and leaving the balloon of Embodiment 1 together with the bone cement and the material activating osteogenesis and/or osteo-induction in the human body.

Therein, the bone cement injected in the step (2) may be in the thin phase, the drawing phase, or the early dough phase. Preferably, it is in the thin phase to give plenty time for operation.

In the steps (3) and (4), a pneumatic pump or a hydraulic pump is connected to the fifth duct 9 and the expansion chamber 109 for maintaining pressure levels therein.

According to the prior art, percutaneous kyphoplasty requires bone cement injected to be in the late drawing phase or the early dough phase. This is because if injection is performed with bone cement in the thin phase, the bone cement is more mobile, and tends to spread out. On the other hand, if injection is performed with bone cement in the late dough phase, the bone cement is insufficiently dispersible, and tends to cause duct blockage. With use of the balloon, the present embodiment eliminates the concern about leakage and dispersion of bone cement, and thereby allows the bone cement injected to be in the thin phase.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. A medical procedure for discoplasty, using a balloon for discoplasty, wherein said balloon comprises a compressed, collapsed or folded balloon body, which contains therein a first chamber, and has a surface provided with a first sprue communicated with the first chamber, wherein when deployed, the balloon body defines a second chamber running therethrough and has a medium inlet channel communicated with the second chamber, in which the balloon body has the surface further provided with a second sprue that is communicated with the medium inlet channel, the medical procedure comprising steps of:
   (1) filling bone cement into the first chamber;
   (2) aligning openings at two ends of the second chamber with intervertebral disc tissue at two sides of the balloon; and
   (3) filling the second chamber with a material or cells activating osteogenesis and/or osteo-induction;
   wherein, the steps (1)-(3) are performed sequentially;
   wherein the balloon body is made of stacked inner and outer layers of a flexible material, and an expansion chamber is formed between the inner and outer layers of the flexible material, in which the outer layer of the flexible material is provided with a pressurizing port that is communicated with the expansion chamber, and a predetermined area between the inner and outer layers of the flexible material is provided with a connecting portion connecting the inner and outer layers of the flexible material, so that filling a pressurized medium into the expansion chamber through the pressurizing port such deploys the balloon body that the deployed balloon body has a ring-like shape with the first chamber defined therein; and
   the medical procedure for discoplasty further comprising a step of:
   (4) filling the expansion chamber with the pressurized medium to deploy the balloon body;
   wherein the step (4) is performed prior to the step (1).

2. The medical procedure for discoplasty of claim 1, wherein:
   the surface of the balloon body of the used balloon is raised to form a fourth duct connected to a peripheral wall of the second sprue, and the fourth duct is provided therein with a plug for preventing a medium from flowing out, in which the plug is a bolt configured to be screwedly engaged with the fourth duct, and the bolt has an outer end provided with a non-rotatable notch or knob for driving the bolt;
   the medical procedure for discoplasty further comprising steps of:
   (5) rotating the bolt to separate the bolt from the fourth duct; and
   (6) rotating the bolt to connect the bolt with the fourth duct;
   wherein, the step (5) is performed prior to the step (3), and is independent of the step (1) and the step (2) in terms of sequence; and
   wherein, the step (6) is performed after the step (3).

* * * * *